United States Patent

Fu

Patent Number: 5,834,459
Date of Patent: *Nov. 10, 1998

[54] ALKYL-SUBSTITUTED COMPOUNDS HAVING DOPAMINE RECEPTOR AFFINITY

[75] Inventor: Jian-Min Fu, Brampton, Canada

[73] Assignee: Allelix Biopharmaceuticals Inc., Ontario, Canada

[*] Notice: The term of this patent shall not extend beyond the expiration date of Pat. Nos. 5,602,121 and 5,602,124.

[21] Appl. No.: 754,014

[22] Filed: Apr. 1, 1996

Related U.S. Application Data

[63] Continuation-in-part of Ser. No. 354,793, Dec. 12, 1994, Pat. No. 5,602,121.

[51] Int. Cl.$^6$ ............ A61K 31/55; C07D 267/20; C07D 413/04; C07D 417/04
[52] U.S. Cl. ............ 514/211; 514/212; 514/217; 514/218; 514/220; 514/255; 514/320; 514/325; 540/484; 540/547; 540/557; 540/575; 540/587; 540/596; 540/609; 544/375; 544/381; 546/196; 546/203; 546/204
[58] Field of Search .................. 540/484, 547, 540/557, 575, 576, 587, 596, 609; 544/359, 375, 381; 546/196, 202, 203, 204; 514/211, 212, 217, 218, 220, 255, 320, 324, 325

[56] References Cited

U.S. PATENT DOCUMENTS

| | | | |
|---|---|---|---|
| 3,458,516 | 7/1969 | Howell et al. | 260/268 |
| 3,501,483 | 3/1970 | Howell et al. | 260/293.4 |
| 3,546,226 | 12/1970 | Schmutz | 260/268 |
| 5,229,382 | 7/1993 | Chakrabarti et al. | 514/220 |
| 5,286,722 | 2/1994 | Cairns et al. | 514/211 |
| 5,393,752 | 2/1995 | Liegeois et al. | 514/211 |
| 5,602,121 | 2/1997 | Fu | 514/211 |
| 5,602,124 | 2/1997 | Tehim et al. | 514/220 |
| 5,605,897 | 2/1997 | Beasley, Jr. et al. | 514/220 |

OTHER PUBLICATIONS

The Merck Manual, Fifteenth Edition, (1987), Berkow, M.D., Editor-in-chief, pp. 2486-2487.

*Primary Examiner*—Richard L. Raymond
*Assistant Examiner*—Deepak R. Rao
*Attorney, Agent, or Firm*—Nikaido Marmelstein Murray & Oram LLP

[57] ABSTRACT

Described herein are D4 receptor-selective compounds of the general formula:

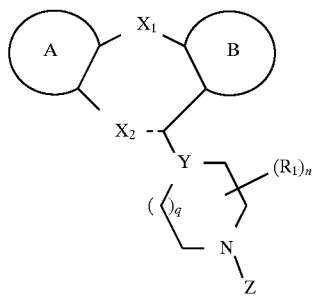

wherein:

A and B are independently selected, optionally substituted, unsaturated 5- or 6-membered, homo- or heterocyclic rings;

$X_1$ is selected from $CH_2$, O, NH, S, C=O, CH—OH, CH—N($C_{1-4}$alkyl)$_2$, C=CHCl, C=CHCN, N—$C_{1-4}$alkyl, N-acetyl, $SO_2$ and SO;

$X_2$ - - - is selected from N=, $CH_2$—, CH= and C(O);

Y is selected from N and CH;

$R_1$ represents $C_{1-4}$alkyl;

n is 0, 1 or 2;

q is 1 or 2; and

Z is $C_{5-10}$alkyl optionally substituted with OH, halo, $C_{1-4}$alkyl or $C_{1-4}$alkoxy and optionally incorporating a heteroatom selected from O, N and S;

and acid addition salts, solvates and hydrates thereof. Their use as ligands for dopamine receptor identification and in a drug screening program, and as pharmaceuticals to treat indications in which D4 receptor stimulation is implicated, such as schizophrenia, is also described.

16 Claims, No Drawings

ALKYL-SUBSTITUTED COMPOUNDS HAVING DOPAMINE RECEPTOR AFFINITY

CROSS REFERENCE TO RELATED APPLICATION

This application is a continuation-in-part of U.S. Ser. No. 08/354,793 filed Dec. 12, 1994 now U.S. Pat. No. 5,602,121.

This invention relates to compounds that bind to the dopamine D4 receptor, to their preparation and their use for therapeutic and drug screening purposes.

BACKGROUND TO THE INVENTION

Neuronal cell receptors that bind the neurotransmitter dopamine constitute a group of at least five structurally distinct proteins that can now be produced using recombinant DNA techniques. These techniques have been applied to construct cell lines that incorporate the dopamine receptor in their membranes, to provide regenerable and homogeneous substrates with which chemical libraries can be screened to identify potential CNS-active drugs.

Recent evidence strongly implicates the dopamine receptor classified as D4 in the etiology of schizophrenia. It has been suggested that compounds capable of interfering with the function of this receptor, which is present in schizophrenics at levels that are six times normal, would be useful in the treatment of this disease (Seeman et al, Nature, 1993, 365:441). Some drugs currently on the market in fact exhibit the desired antagonism of D4 receptor activity, and bind with relative strong affinity to the receptor. Yet because of their structure, these drugs interact also with related dopamine receptors, particularly the D2 receptor type, which results in significant side effects that include altered motor function and tachycardia. It would be desirable to provide compounds that exhibit not only a high degree of affinity for the D4 receptor, but also a relatively low degree of affinity for the D2 receptor. In this specification, this desired combination of receptor binding properties is referred to as D4 selectivity.

Products currently marketed to treat indications in which the D4 receptor function is implicated include the dibenzodiazepine, clozapine, and the dibenzoxazepine, isoloxapine. Analysis of their dopamine receptor binding properties has shown that the preference for binding the D4 receptor relative to the D2 receptor is about 10 fold, for both products. Similarly, both bind the D4 receptor with about the same affinity (Ki value approximately 20 nM). Other products, recently published in the scientific literature, have shown similar D4 to D2 selectivity profile and D4 affinity values.

It is an object of the present to provide a compound that binds to the D4 receptor selectively relative to the D2 receptor.

It is an object of the present invention to provide a compound having an improved D4 selectivity profile.

It is another object of the present invention to provide a compound having an improved D4 binding affinity.

It is another object of the present invention to provide a compound having both an improved D4 selectivity profile and D4 binding affinity.

It is a further object of the present invention to provide a pharmaceutical composition comprising a compound of the present invention, as active ingredient.

SUMMARY OF THE INVENTION

According to one aspect of the present invention, there is provided a compound of Formula I:

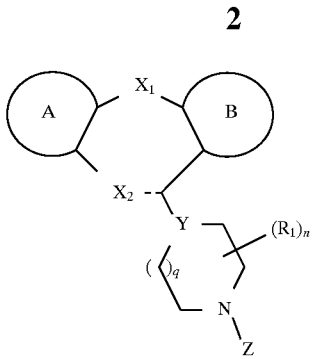

wherein:
A and B are independently selected, optionally substituted, saturated 5- or 6-membered, homo- or heterocyclic rings;

X is selected from O, S, SO, $SO_2$, $CH_2$ CH—OH, CH—N($C_{1-4}$alkyl)$_2$, C=CHCl, C=CHCN, C=O, NH, N—$C_{1-4}$alkyl and N-acetyl;

$X_2$ - - - is selected from N=, $CH_2$—, CH= and C(O)—;

Y is selected from N and CH;

$R_1$ represents $C_{1-4}$alkyl;

n is 0, 1 or 2;

q is 1 or 2; and

Z is $C_{5-10}$alkyl optionally substituted with OH, halo, $C_{1-4}$alkyl or $C_{1-4}$alkoxy and optionally incorporating a bridging heteroatom selected from O, N and S;

and acid addition salts, solvates and hydrates thereof.

According to another aspect of the invention, there is provided a pharmaceutical composition comprising a compound of Formula I and a pharmaceutically acceptable carrier.

In a further aspect of the invention, there is provided an analytical method in which a compound of the invention is used either to distinguish the D4 receptor from other receptor types or from the D2 receptor.

These and other aspects of the present invention are now described in greater detail hereinbelow.

DETAILED DESCRIPTION AND PREFERRED EMBODIMENTS

The invention relates to compounds that bind the dopamine D4 receptor in a selective manner, relative to the dopamine D2 receptor. It has been found, more particularly, that the D4 selectivity of D4-binding ligands having the tricyclic structure:

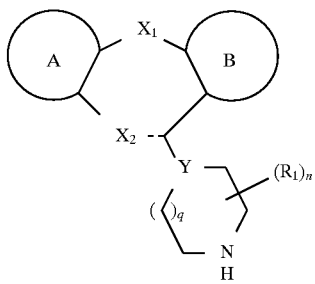

can be significantly improved when the piperazine group is derivatized by an alkyl group designated Z. In accordance with one of its aspects, the present invention accordingly provides compounds that conform to Formula I:

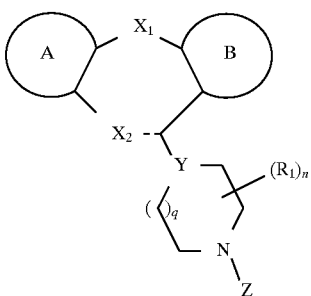

In embodiments of the invention, Z is $C_{5-10}$alkyl optionally substituted with OH, halo, $C_{1-4}$alkyl or $C_{1-4}$alkoxy and optionally incorporating 1, 2 or 3, eg. 1 or 2, heteroatom selected from O, N and S. Particular embodiments of the invention include those in which Z is hexyl, octyl or nonyl optionally substituted with OH, halo, $C_{1-4}$alkyl or $C_{1-4}$alkoxy and optionally incorporating a heteroatom bridge member selected from O, N and S. In specific embodiments of the invention, Z is selected from hexyl and nonyl. In the case where Z is substituted, typically 1 or 2 substitutions can be made, desirably either at the proximal, mid, or distal carbons of Z. Particularly suitable substituents include —OH, —Cl, methyl, ethyl and methoxy.

The tricyclic function to which Z is coupled can have various structures and will typically incorporate those found to be important for dopamine D4 receptor binding. In other words, the tricycles suitable for coupling to Z are those which, when substituted by functions other than Z, are determined by the assay herein described, to bind the D4 receptor (preferably the human D4 receptor) with an affinity not greater than 1 μM (Ki). In particular, the rings A and B are selected, according to embodiments of the invention, from benzene, pyridine, pyrimidine, pyrazine, pyridazine, pyrole, imidazole, triazole, pyrazole, thiophene, thiazole, and pyran. In a particular embodiment, ring A is selected from benzene and pyridine and ring B is selected from benzene, pyridine, pyrimidine, pyrazine, pyridazine, pyrole, imidazole, triazole, pyrazole, thiophene, thiazole, furan and pyran; and is particularly selected from benzene and pyridine. In specific embodiments of the invention, both rings A and B are benzene. It is to be appreciated that when rings A and B are heterocycles, the heteroatoms are shared with the central seven membered ring only when the shared heteroatom is N. Such tricycles are within the scope of the Formula I; one embodiment of which is described by Lednicer et al in *The Organic Chemistry of Drug Synthesis*, (1992, John Wiley & Sons Inc., New York) wherein ring B is imidazole that is fused to a thiazepine at one of the imidazole nitrogen atoms.

One or both rings A and B may be substituted with from 1 to 3, usually 1 or 2, substituents. When substituted, the substituents are selected from hydroxyl, halo, $C_{1-4}$alkyl, amino, nitro, cyano, halo-substituted $C_{1-4}$alkyl, $C_{1-4}$alkoxy, halo-substituted $C_{1-4}$alkoxy, $C_{1-4}$alkoxycarbonyl, $C_{1-4}$acyl, halo-substituted $C_{1-4}$acyl, cyclo-$C_{3-7}$alkyl, thio-$C_{1-4}$alkylene, $C_{1-4}$alkylthio, halo-substituted $C_{1-4}$alkylthio, cyanothio, tetrazolyl, N-piperidinyl, N-piperazinyl, N-morpholinyl, acetamido, $C_{1-4}$ alkylsulfonyl, halosulfonyl, halo-substituted $C_{1-4}$alkylsulfonyl, $C_{1-4}$alkylsulfoxyl, sulfonamido, $C_{1-4}$alkylseleno, and $OSO_3H$.

Substitution sites on rings A and B will be limited in practice to the carbon atoms on the ring that are not shared with the central seven membered ring. For example, a benzene ring can accomodate up to 4 substituents; pyridine, and pyran rings can accomodate up to 3 substituents; pyrimidine, pyrazine, pyridazine, pyrole, furan and thiophene rings can accomodate up to 2 substituents; imidazole, pyrazole and thiazole rings can accomodate only 1 substituent; and a triazole ring can accomodate no substituents. It is also to be understood that rings A and B may incorporate substituents at nitrogen atoms on the ring that are not shared with the central seven membered ring. For example the NH member of an imidazole ring may be substituted. In particular embodiments, rings A and B are substituted with from 1 to 2 substituents selected from chloro, fluoro, methyl, trifluoromethyl, methoxy, nitro, cyano and methylthio. In particularly preferred embodiments ring A is benzene substituted with 1 or 2 substituents selected from chloro, methyl, nitro and cyano and ring B is benzene substituted with 1 or 2 substituents selected from chloro, methoxy, trifluoromethyl and nitro.

In the central, 7-membered ring of the tricycle, $X_1$ may be any one of $CH_2$, O, NH, S, C=O, CH—OH, CH—N($C_{1-4}$alkyl)$_2$, C=CHCl, C=CHCN, N—$C_{1-4}$alkyl, N-acetyl, $SO_2$ and SO, while $X_2$ - - - may be any one of N=, $CH_2$—, CH=, C(O)—, O—, and S—. In a particular embodiment of the invention, $X_1$ is O, S or NH. In another embodiment, $X_2$ - - - is N= or CH=. In a particularly preferred embodiment, $X_1$ is O, S or NH and $X_2$ - - - is N= or CH=. In specific embodiments $X_1$ and $X_2$ - - - are selected to form a seven membered ring selected from oxazepine, diazepine, thiazepine and thiepine.

In preferred embodiments $X_1$ and $X_2$ - - - together with rings A and B are selected to form a tricycle that is selected from 5H-dibenzo[b,e][1,4]diazepine that is optionally substituted, for example with one of 7,8-dichloro, 7,8-dimethyl, 2-chloro, 3-chloro, 4-chloro, 2,4-dichloro, 4,7,8-trichloro, 2-trifluoromethyl, 1-fluoro, or 2-methoxy; dibenz[b,f][1,4]oxazepine that is optionally substituted, for example with one of 4-nitro, 8-chloro, 4-cyano or 4-chloro; dibenzo[b,f]thiepine that is optionally substituted, for example with one of 2-nitro or 2-chloro; 11H-dibenzo[b,f] thiepine that is optionally substituted, for example with 2-methylthio; and dibenzo[b,f][1,4]thiazepine that is optionally substituted, for example with 8-chloro. In a specific embodiment of the invention, $X_1$ and $X_2$ - - - together with rings A and B are selected to form a tricycle that is selected from:

dibenz[b,f][1,4]oxazepine;
4-chlorodibenz[b,f][1,4]oxazepine; and
8-chlorodibenz[b,f][1,4]oxazepine.

In a most preferred embodiment, $X_1$ and $X_2$ - - - together with rings A and B form a tricycle that is 8-chloro-dibenz [b,f][1,4] oxazepine.

In an embodiment of the invention, the N-containing ring coupled to the tricyclic structure may incorporate 0, 1 or 2 $R_1$ substituents that are $C_{1-4}$alkyl groups, such as methyl. The piperazinyl ring may incorporate an additional $CH_2$ group (q=2) to form a diazepine ring as described by Horrom et al (U.S. Pat. No. 4,096,261). In another embodiment of the invention, Y is N thereby forming a piperazine or imidazolidine ring or Y is CH thereby forming a pyrrolidine or piperidine ring, depending on the value of q. In particular embodiments of the invention, n is 0; q is 1 and Y is N. In a specific embodiment n, q and Y are chosen to give an unsubstituted piperazinyl ring.

In a particular embodiment of the invention, there are provided compounds of formula (I) that bind to the D4 receptor selectively relative to the D2 receptor, including:

11-(4-hexyl-1-piperazinyl) dibenz[b,f][1,4]oxazepine;
11-(4-heptyl-1-piperazinyl) dibenz[b,f][1,4]oxazepine; and 11-(4-octyl-1-piperazinyl) dibenz[b,f][1,4]oxazepine;

11-(4-nonyl-1-piperazinyl) dibenz[b,f][1,4]oxazepine; and 4-chloro-11-(4-hexyl-1-piperazinyl)dibenz[b,f][1,4] oxazepine;

4-chloro-11-(4-nonyl-1-piperazinyl)dibenz[b,f][1,4] oxazepine.

8-chloro-11-(4-nonyl-1-piperazinyl)dibenz[b,f][1,4] oxazepine;

In a more preferred embodiment, there are provided compounds of formula (I) exhibiting better D4 selectivity than clozapine, including:

8-chloro-11-(4-nonyl-1-piperazinyl)dibenz[b,f][1,4] oxazepine;

4-chloro-11-(4-nonyl-1-piperazinyl)dibenz[b,f][1,4] oxazepine;

11-(4-hexyl-1-piperazinyl) dibenz[b,f][1,4]oxazepine; and 4-chloro-11-(4-hexyl-1-piperazinyl)dibenz[b,f][1,4] oxazepine.

In a most preferred embodiment, there are provided compounds of formula (I) exhibiting better D4 affinity and selectivity than clozapine, including:

8-chloro-11-(4-nonyl-1-piperazinyl)dibenz[b,f][1,4] oxazepine; and 11-(4-hexyl-1-piperazinyl) dibenz[b,f][1,4]oxazepine.

Acid addition salts of the compound of Formula I include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for ligand use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

It will be appreciated that certain compounds of Formula I may contain an asymmetric centre. Such compounds will exist as two (or more) optical isomers (enantiomers). Both the pure enantiomers and the racemic mixtures (50% of each enantiomer), as well as unequal mixtures of the two, are included within the scope of the present invention. Further, all diastereomeric forms possible (pure enantiomers and mixtures thereof) are within the scope of the invention.

The compounds of the present invention can be prepared by processes analogous to those known in the art. The present invention therefore provides, in a further aspect, a process for the preparation of a compound of Formula I or a salt, solvate or hydrate thereof, which comprises the step of coupling a reagent of Formula A:

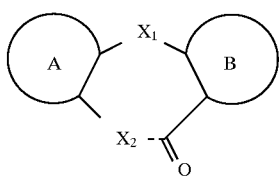

with a reagent of Formula B:

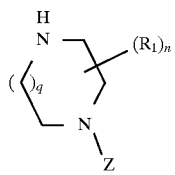

using a Lewis acid such as $TiCl_4$ or $BF_3.Et_2O$.

Reagent (A) can be obtained commercially or can be synthesized using established ring closure procedures. For example, when $X_1$ is NH and $X_2$ - - - is N= (a diazepine), reagent (A) may be prepared according to the procedures described by Giani et al (Synthesis, 1985, 550) by refluxing equimolar amounts of 2-chlorobenzoic acid, o-phenylenediamine and powdered copper in chlorobenzene. The following is a schematic representation of the reaction to obtain the diazepine form of reagent (A):

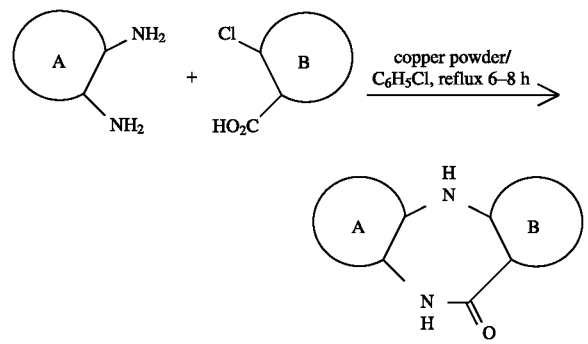

When $X_1$ is O and $X_2$ - - - is N= (an oxazepine), reagent (A) may be prepared according to the procedures described by Klunder (J. Med. Chem. 1992, 35:1887) by condensation of a 2-aminophenol with 2-chloro-5-nitrobenzoyl chloride in THF to afford the corresponding carboxamide followed by refluxing with NaOH for ring closure. The following is a schematic representation of the steps to obtain the oxazepine form of reagent (A):

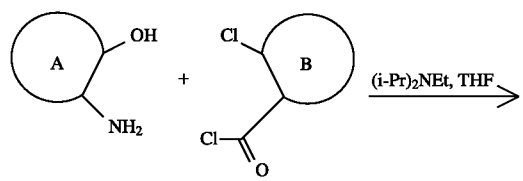

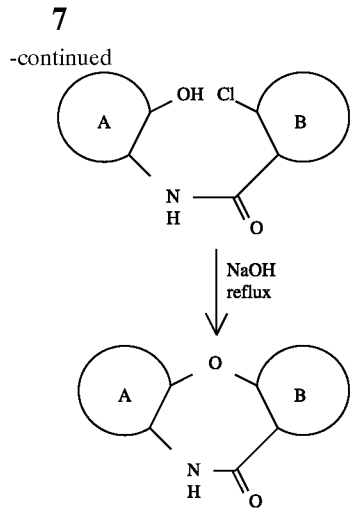

The thiepine form of reagent (A), i.e. when $X_1$ is S and $X_2$ - - - is CH=, may be prepared according to the procedures described by Sindelar et al (Collect. Czech. Chem. Commun, 1983, 48(4):1187). When reagent (A) is an oxepine i.e. when $X_1$ is O and $X_2$ - - - is $CH_2$—, it may be prepared in the manner reported by Harris et al (J. Med. Chem., 1982, 25(7):855); and the corresponding cycloheptene reagent (A) i.e. when $X_1$ and $X_2$ - - - are both $CH_2$, may be prepared as reported by De Paulis et al (J. Med. Chem. 1981, 24(9):1021). The thiazepine reagent (A) may be prepared in a four step process starting from 1-bromo-2-nitrobenzene and methyl thiosalicylate. The steps involve coupling; reduction of the nitro group; hydrolysis of the ester group; and finally ring closure.

Many of the reagents of Formula B are similarly available from various commercial sources. In the alternative, or where the desired reagent is not commercially available, reagent B can be synthesized from the corresponding 1-piperazinecarboxyaldehyde by reaction with Halo-Z, where halo is desirably the bromo derivative. Halo-substituted $C_{5-10}$alkyl compounds are commercially available such as 1-bromohexane and 1-bromononane or may be synthesized using established synthetic techniques.

In the specific case where Y=CH, synthesis proceeds by coupling isonicotinic acid (4-$C_{5-10}$alkyl derivative thereof) with an amino reagent of the formula:

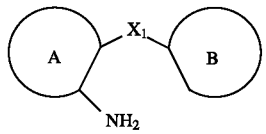

using a suitable coupling agent such as EDCl, to form an amide intermediate. The amino reagent may be obtained commercially or may be synthesized according to established synthetic techniques. For example, 2-chloronitrobenzene can be converted to the amino reagent 2-aminodiphenylsulphide (or oxide) by substitution with thiobenzene (or hydroxybenzene) in the presence of $K_2CO_3$ and then reducing in the presence of Zn. The resulting amide intermediate can then be cyclized with a suitable ring closure agent such as $POCl_3$ to give the final compound according to formula I wherein Y is CH.

For use as a ligand, the present compounds can be stored in packaged form for reconstitution and use. The compounds can be used to distinguish dopamine receptors from other receptor types, for example glutamate and opioid receptors, within a population of receptors and in particular to distinguish between the D4 and D2 receptors. The latter can be achieved by incubating preparations of the D4 receptor and of the D2 receptor with a D4 selective compound of the invention and then incubating the resulting preparation with a radiolabelled dopamine receptor ligand, such as $^3$H-spiperone. The D2 and D4 receptors are then distinguished by determining the difference in membrane-bound radioactivity, with the D4 receptor exhibiting lesser radioactivity, i.e., lesser $^3$H-spiperone binding.

In another embodiment of the invention, the compound is provided in labelled form, such as radiolabelled form e.g. labelled by incorporation within its structure of $^3$H or $^{14}$C or by conjugation to $^{123}$I or 125I. Such radiolabelled forms can be used to directly to distinguish between dopamine D4 and dopamine D2 receptors. Furthermore, radiolabelled forms of the present compounds can be exploited to screen for more potent dopamine D4 ligands, by determining the ability of the test ligand to displace the radiolabelled compound of the present invention.

The clozapine-like binding profile of the present compounds indicates their utility as pharmaceuticals that may be useful for the treatment of various conditions in which the use of a dopamine D4 receptor antagonist is indicated, such as for the treatment of anxiety and schizophrenia.

For use in medicine, the compounds of the present invention are usually administered in a standard pharmaceutical composition. The present invention therefore provides, in a further aspect, pharmaceutical compositions comprising an effective amount of a compound of Formula I or a pharmaceutically acceptable salt, solvate or hydrate thereof and a pharmaceutically acceptable carrier.

The compounds of the present invention may be administered by an convenient route, for example by oral, parenteral, buccal, sublingual, nasal, rectal or transdermal administration and the pharmaceutical compositions formulated accordingly.

The compounds and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as flurochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine.

Compositions for rectal administration are conveniently in the form of suppositories containing a conventional suppository base such as cocoa butter.

Preferably, the composition is in unit dose form such as a tablet, capsule or ampoule. Suitable unit doses i.e. therapeutically effective amounts; can be determined during clinical trials designed appropriately for each of the conditions for which administration of a chosen compound is indicated and will of course vary depending on the desired clinical endpoint. It is anticipated that dosage sizes appropriate for administering the compounds of the examples will be roughly equivalent to, or slightly less than, those used currently for clozapine. Accordingly, each dosage unit for oral administration may contain from 1 to about 500 mgs, and will be administered in a frequency appropriate for initial and maintenance treatments.

EXAMPLE 1 a) 11-(4-hexyl-1-piperazinyl)dibenz[b,f][1,4]oxazepine

The starting material 10,11-dihydro-dibenz[b,f][1,4]oxazepin-11-one was prepared according to the procedures reported in Coyne et al (J. Med. Chem., 1967, 10:541). Briefly, this entailed coupling potassium salicylaldehyde with 2-chloronitrobenzene, followed by oxidation to the carboxylic acid, reduction of nitro, and finally ring closure, to yield the desired starting material.

To a stirred solution of 10,11-dihydro-dibenz[b,f][1,4]oxazepin-11-one in dry toluene at room temperature was added piperazine (Aldrich) followed by the dropwise addition of $TiCl_4$. The reaction mixture was refluxed for 2 hours, cooled to room temperature and then poured into an ammonium hydroxide solution. The resulting mixture was extracted with dichloromethane, and the combined organic phases were then dried ($K_2CO_3$) and concentrated. Purification of the product was conducted on silica gel using ethyl acetate:hexane (5:1→4:1) as the eluant to give 11-(1-piperazinyl)dibenz[b,f][1,4]oxazepine.

To a stirred solution of 11-(1-piperazinyl)dibenz[b,f][1,4]oxazepine (0.28 g, 1.00 mmol) in DMF (10 mL) was added sodium hydride (0.056 g, 60% in oil, 1.40 mmol) at 0° C. under argon. The mixture was stirred at 0° C. for 10 min at room temperature for 20 minutes, and then treated with 1-bromohexane (0.198 g, 1.2 mmol). The resulted mixture was stirred at room temperature overnight and quenched with saturated ammonium chloride solution (10 mL). The mixture was extracted with ethyl acetate (3×30 mL). The combined organic phase was dried over magnesium sulfate and filtered. The filtrate was concentrated in vacuo to dryness and the residue was subjected to column chromatography using ethyl acetate/hexane (1/2) as the eluent. The desired compound, 11-(4-hexyl-1-piperazinyl)dibenz[b,f][1,4]oxazepine, was obtained in 0.167 g (46%) as a light yellow oil.

The maleic acid salt of the title compound was subsequently prepared by the following procedures: To a solution of 11-(4-hexyl-1-piperazinyl)dibenz[b,f][1,4]oxazepine (0.14 g, 0.39 mmol) in diethyl ether (2.0 mL) was added the solution of maleic acid (0.05 g, 0.43 mmol) in methanol (0.5 mL). The mixture was stirred at room temperature for 30 minutes and concentrated in vacuo to dryness. The residue was triturated with diethyl ether and filtered. The maleic salt was obtained as a white solid (0.088 g, 47%), m.p. 89°–92° C.; MS 364 ($M^+$—$C_4H_4O_4$+1).

In a like manner, there were prepared the following additional compounds:

b) 11-(4-heptyl-1-piperazinyl)dibenz[b,f][1,4]oxazepine, from 11-(1-piperazinyl)dibenz[b,f][1,4]oxazepine (0.28 g, 1.00 mmol) and 1-bromoheptane (0.24 mL, 0.27 g, 1.5 mmol) with NaH (0.048 g, 60% in oil, 1.2 mmol). The desired product was obtained in 0.29 g (78%), oil.

MS: 378.28 ($M^+$+1);

c) 11-(4-octyl-1-piperazinyl)dibenz[b,f][1,4]oxazepine, from 11-(1-piperazinyl)dibenz[b,f][1,4]oxazepine (0.28 g, 1.00 mmol) and 1-bromooctane (0.24 mL, 0.29 g, 1.5 mmol) with NaH (0.048 g, 60% in oil, 1.2 mmol). The desired product was obtained in 0.24 g (62%), oil.

MS: 392.27 ($M^+$+1);

d) 11-(4-nonyl-1-piperazinyl)dibenz[b,f][1,4]oxazepine, 49%, oil. The maleic acid salt, 72%, m.p. 128°–130° C., MS 406 ($M^+$—$C_4H_4O_4$+1);

e) 4-chloro-11-(4-hexyl-1-piperazinyl)dibenz[b,f][1,4]oxazepine, 71%, oil. The maleic acid salt, 89%, m.p. 168°–170° C., MS 397 ($M^+$—$C_4H_4O_4$+1); and f) 4-chloro-11-(4-nonyl-1-piperazinyl)dibenz[b,f][1,4]oxazepine, 67%, oil. The maleic acid salt, 85%, m.p. 134°–136° C., MS 441 ($M^+$—$C_4H_4O_4$+1).

EXAMPLE 2 a) 8-chloro-11-(4-nonyl-1-piperazinyl)dibenz[b,f][1,4]oxazepine.

A mixture of 1-benzyl-4-nonylpiperazine (0.54 g, 1.80 mmol) (prepared by reacting 1-benzylpiperazine, Aldrich, with 1-bromononane, Aldrich, and NaH in DMF), palladium hydroxide on carbon (0.14 g) and cyclohexene (7 mL) in ethanol (15 mL) was heated at reflux overnight. After filtration, the filtrate was concentrated in vacuo to dryness to give 1-nonylpiperazine as an oil, 0.38 g, 100%.

8-chloro-10,11-dihydrodibenz[b,f][1,4]oxazepin-11-one was next prepared according to the procedures reported in Coyne et al (J. Med. Chem., 1967, 10:541). Briefly, this entailed coupling potassium salicylaldehyde with 2,5-dichloronitrobenzene, followed by oxidation to the carboxylic acid, reduction of nitro, and finally ring closure, to yield the desired 8-chloro starting material.

To a stirred solution of 8-chloro-10,11-dihydrodibenz[b,f][1,4]oxazepin-11-one (0.53 g, 2.15 mmol) in toluene (20 mL) was added phosphorus pentachloride (0.54 g, 2.58 mmol) at room temperature under argon. The resulting mixture was heated at reflux for 4 h and the solvent was removed in vacuo. The residue was redissolved in toluene and reconcentrated. The light yellow solid 8,11-dichlorodibenz[b,f][1,4]oxazepine (0.51 g, quantitative yield) was used directly for the next reaction without further purification.

The mixture of 8,11-dichlorodibenz[b,f][1,4]oxazepine (0.32 g, 1.19 mmol), 1-nonylpiperazine (0.38 g, 1.79 mmol) and 1,8-diazabicyclo[5.4.0]undec-7-ene (DBU) (0.72 mL, 0.73 g, 4.77 mmol) in acetonitrile (15 mL) was heated at reflux for 6 h. After the mixture was concentrated, water (20 mL) and ethyl acetate (20 mL) were added. The two phases were separated and the aqueous phase was extracted with ethyl acetate (2×20 mL). The combined ethyl acetate solution was dried over magnesium sulfate and filtered. The filtrate was then concentrated in vacuo to dryness and the residue was subjected to column chromatography using ethyl acetate/hexane (1/2) as the eluent. The compound 8-chloro-11-(4-nonyl-1-piperazinyl)dibenz[b,f][1,4]oxazepine was obtained as a white solid (0.15 g, 28%), m.p. 64°–66° C., MS 440 ($M^+$+1).

In a like manner there are prepared the following additional Formula I compounds:

b) 8-chloro-11-(4-hexyl-1-piperazinyl)dibenz[b,f][1,4]oxazepine; from 1-bromohexane;
c) 8-chloro-11-(4-heptyl-1-piperazinyl)dibenz[b,f][1,4]oxazepine; from 1-bromoheptane; and
d) 8-chloro-11-(4-octyl-1-piperazinyl)dibenz[b,f][1,4]oxazepine; from 1-bromooctane;

EXAMPLE 3

4-Chloro-11-(4-hexyl-1-homopiperazinyl)dibenz[b,f][1,4]oxazepine

In a like manner as Example 1, 4-Chloro-10,11-dihydro-dibenz[b,f][1,4]oxazepine-11-one (2.46 g, 10.0 mmol) was reacted with homopiperazine (7.41 g, 74.0 mmol) in the presence of titanium tetrachloride (2.09 g, 11.0 mmol) in toluene (55.0 mL) and anisole (2.00 mL) to produce 4-Chloro-11-(1-homopiperazinyl)dibenz[b,f][1,4]oxazepine; viscous oil; yield, 0.92 g (28%). This crude product (0.26 g, 0.79 mmol) was reacted with 1-bromohexane (0.13 mL, 0.16 g, 0.95 mmol) in the presence of sodium hydride (0.044 mg, 60% in oil, 1.11 mmol) in DMF (10.0 mL) to produce 4-Chloro-11-(4-hexylhomopiperazinyl)dibenz[b,f][1,4]oxazepine; viscous oil; yield, 0.17 g (52%).

MS (FAB) 412 ($m^+$+1).

EXAMPLE 4

Receptor Binding Assay

D2 and D4 receptor-binding affinities of compounds of Examples 1 and 2 were evaluated according to their ability to reduce binding of $^3$H-spiperone as compared to the reference compound clozapine. The potency of the test compound to reduce $^3$H-spiperone binding directly correlated to its binding affinity for the receptor.

D4 Receptor Preparation

HEK 298 (human embryonic kidney) cells stably transfected with human D4 receptor (D4.2 sub-type) were grown in NUNC cell factories for 5 days (75% confluency) without a media change and removed with versene (approximately 19 mg of cells per cell factory tray). The cells were then centrifuged in a Sorval centrifuge for 10 minutes, 5000 rpm (GS3 rotor) and the pellets quickly frozen in liquid nitrogen and stored at –80° C. until used in binding assay. When used in the assay, cells were thawed on ice for 20 minutes and then 10 mL of incubation buffer (50 mM Tris, 1 mM EDTA, 4 mM $MgCl_2$, 5 mM KCl, 1.5 mM $CaCl_2$, 120 mM NaCl, pH7.4) was added. The cells were then vortexed to resuspend pellet and homogenized with a Kinematica CH-6010 Kriens-LU homogenizer for 15 seconds at setting 7. Concentration of receptor protein was determined using the Pierce BCA assay.

D2 Receptor Preparation $GH_4C_1$ (rat pituitary) cells stably transfected with the human D2 receptor (short isoform) were grown in $CO_2$ independent media in roller bottles (1500 $cm^2$) for 10 days. 100 $\mu$M $ZnSO_4$ was added to the cells (the D2 promoter being zinc inducible). After 16 hours, fresh media was added to allow the cells to recover for 24 hours. The cells were harvested using versene and then centrifuged in a Sorval centrifuge for 10 minutes, at 5000 rpm (GS3 rotor). Pellets were quickly frozen in liquid nitrogen and stored at –80° C. until used in the binding assays. When used in the assay, cells were thawed on ice for 20 minutes. Each roller bottle produced approximately 72 mg of protein. 10 mL of incubation buffer was added to the pellets which were then vortexed, resuspended and homogenized with a Kinematica CH-6010 Kriens-LU homogenizer for 15 seconds at setting 7. The receptor protein concentration was determined using the Pierce BCA assay.

Total Spiperone Binding Assay

The incubation was started by the addition of 500 $\mu$l (50 $\mu$g protein) membrane homogenate to a solution of 900 $\mu$l incubation buffer and 100 $\mu$l (0.25 nM final conc.) $^3$H-spiperone (90 Ci/mmol Amersham diluted in borosilicate glass vial) in 12×75 mm polypropylene tubes. The tubes were vortexed and incubated at room temperature for 90 minutes. The binding reaction was stopped by filtering using a Brandell Cell Harvester. The samples were filtered under vacuum over glass fibre filters (Whatman GF/B) presoaked for 2 hours in 0.3% polyethylenimine (PEI) in 50 mM Tris buffer (pH7.4). The filters were then washed 3 times with 5 mL ice cold 50 mM Tris buffer (pH7.4). Individual filter disks were put in scintillation vials (Biovials, Bechman). Ready Protein Plus liquid scintillant (5 mL, Beckman) was added and the vials counted by liquid scintillation spectrophotometry (Beckman LSC 6500) after equilibrating for three hours at room temperature to determine total binding ($B_T$).

Non-Specific Binding Assay for D4

The incubation was started by the addition of 500 $\mu$l (50 $\mu$g protein) membrane homogenate to a solution of 400 $\mu$l incubation buffer, 100 $\mu$l $^3$H-spiperone (90 Ci/mmol Amersham diluted in borosilicate glass vial to 0.25 nM final conc.) and 500 $\mu$l (30 $\mu$M final conc.) of fresh dopamine (Research Biochemicals Inc., light protected and dissolved in incubation buffer) in 12×75 mm polypropylene tubes. The tubes were vortexed and incubated at room temperature for 90 minutes at which time the binding reaction was stopped by filtering. The filters were washed and counted using the same procedure as in the total binding assay described above to give the non-specific binding value (NSB).

Non-Specific Binding Assay for D2

This assay employed the same procedures as the non-specific binding assay for D4 with the exception that 2 $\mu$M (final conc.) of (–) sulpiride (Research Chemicals Inc.) was used in place of dopamine.

Displacement Binding Assay

The incubation was started by the addition to 12×75 mm polypropylene tubes 500 $\mu$l (50 $\mu$g protein) membrane homogenate to a solution of 400 $\mu$l incubation buffer, 100 $\mu$l (0.25 final conc.) $^3$H-spiperone (90 Ci/mmol, Amersham, diluted in borosilicate glass vial to) and 500 $\mu$p of test compound that was prepared from 1 mM stock dissolved in DMSO and stored at –20° C. in polypropylene cryogenic storage vials until dilution in incubation buffer in borosilicate glass vials. The tubes were vortexed and incubated at room temperature for 90 minutes at which time the binding reaction was stopped by filtering. The filters were washed and counted using the same procedure as in the total binding assay described above to give the displacement binding value ($B_D$).

Calculations

The test compounds were initially assayed at 1 and 0.1 $\mu$M and then at a range of concentrations chosen such that the middle dose would cause about 50% inhibition of $^3$H-spiperone binding. Specific binding in the absence of test compound ($B_O$) was the difference of total binding ($B_T$) minus non-specific binding (NSB) and similarly specific binding (in the presence of test compound) (B) was the difference of displacement binding ($B_D$) minus non-specific binding (NSB). $IC_{50}$ was determined from an inhibition response curve, logit-log plot of $\%B/B_O$ vs concentration of test compound.

Ki was calculated by the Cheng and Prustoff transformation:

$$Ki=IC_{50}/(1+[L]/K_D)$$

where [L] is the concentration of $^3$H-spiperone used in the assay and $K_D$ is the dissociation constant of $^3$H-spiperone determined independently under the same binding conditions.

Assay results are reported in the following Table:

| | D4 AFFINITY AND SELECTIVITY | | |
|---|---|---|---|
| COMPOUND | STRUCTURE | Ki | D2/D4 |
| clozapine | 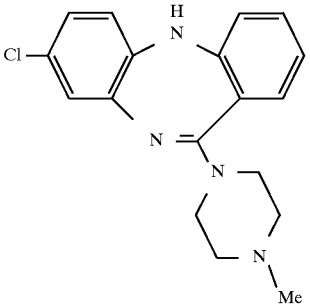 | 23 | 10 |
| 8-chloro-11-(4-nonyl-1-piperazinyl)dibenz[b,f][1,4]oxazepine | 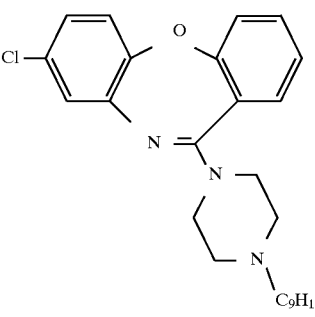 | 18 | 30.0 |
| 11-(4-hexyl-1-piperazinyl)dibenz[b,f](1,4)oxazepine | 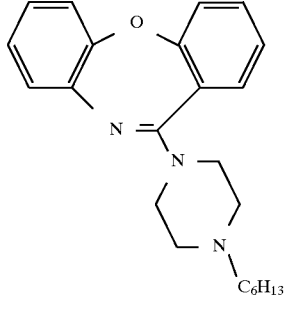 | 22 | 20.0 |
| 4-chloro-11-(4-hexyl-1-piperazinyl)dibenz[b,f][1,4]oxazepine | 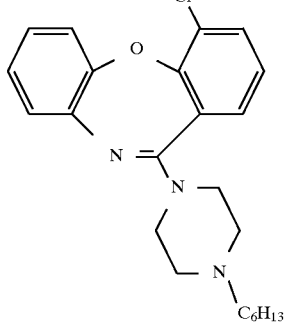 | 32 | 31.8 |

D4 AFFINITY AND SELECTIVITY

| COMPOUND | STRUCTURE | Ki | D2/D4 |
|---|---|---|---|
| 11-(4-nonyl-1-piperazinyl)dibenz[b,f][1,4]oxazepine | 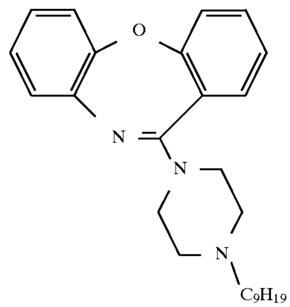 | 109 | 3.9 |
| 4-chloro-11-(4-nonyl-1-piperazinyl)dibenz[b,f][1,4]oxazepine | | 229 | 3.9 |

We claim:

1.

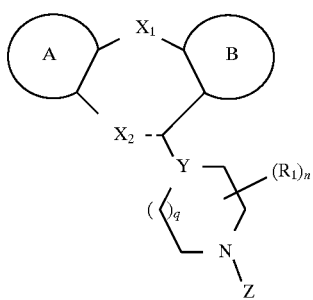

wherein:

A and B are benzene, each independently unsubstituted or optionally substituted with a 4-chloro, 8-chloro, or 8,11-dichloro;

$X_1$ is selected from O, C=O, $CH_2$, CH—OH, CH—N$(C_{1-4}alkyl)_2$, C=CHCl, C=CHCN, NH, N—$C_{1-4}$alkyl and N-acetyl;

$X_2$ - - - is selected from N=, $CH_2$—, CH= and C(O)—;

Y is selected from N and CH;

$R_1$ represents $C_{1-4}$alkyl;

n is 0, 1 or 2;

q is 1 or 2; and

Z is $C_{6-9}$alkyl;

and acid addition salts, solvates and hydrates thereof.

2. A compound according to claim 1, wherein Z is linear $C_{6-8}$alkyl.

3. A compound according to claim 2, wherein Z is hexyl.

4. A compound according to claim 2, wherein Z is heptyl.

5. A compound according to claim 2, wherein Z is octyl.

6. A compound according to claim 1, wherein n is 0.

7. A compound according to claim 6, wherein q is 1.

8. A compound according to claim 1, selected from the group consisting of:

11-(4-hexyl-1-piperazinyl)dibenz[b,f][1,4]oxazepine;
11-(4-heptyl-1-piperazinyl)dibenz[b,f][1,4]oxazepine;
11-(4-octyl-1-piperazinyl)dibenz[b,f][1,4]oxazepine;
11-(4-nonyl-1-piperazinyl)dibenz[b,f][1,4]oxazepine;
4-chloro-11-(4-hexyl-1-piperazinyl)dibenz[b,f][1,4]oxazepine;
8-chloro-11-(4-heptyl-1-piperazinyl)dibenz[b,f][1,4]oxazepine:
8-chloro-11-(4-octyl-1-piperazinyl)dibenz[b,f][1,4]oxazepine:
4-chloro-11-(4-hexyl-1-homopiperazinyl)dibenz[b,f][1,4]oxazepine;
4-chloro-11-(4-nonyl-1-piperazinyl)dibenz[b,f][1,4]oxazepine; and
8-chloro-11-(4-nonyl-1-piperazinyl)dibenz[b,f][1,4]oxazepine.

9. A compound according to claim 8, which is 11-(4-hexyl-1-piperazinyl)dibenz[b,f][1,4]oxazepine.

10. A compound according to claim 8, which is 4-chloro-11-(4-hexyl-1-piperazinyl)dibenz[b,f][1,4]oxazepine.

11. A pharmaceutical composition, comprising a compound according to claim 1 in an amount effective to antagonize D4 receptor stimulation, and a pharmaceutically acceptable carrier.

12. A pharmaceutical composition, comprising a compound according to claim 1 in an amount sufficient to produce an anti-schizophrenia, and a pharmaceutically acceptable carrier.

13. A pharmaceutical composition, comprising a compound according to claim 1 in an amount sufficient to produce an anti-anxiety effect, and a pharmaceutically acceptable carrier.

14. A method of treating a medical condition mediated by D4 receptor stimulation in a patient in need thereof, comprising administering to the patient a D4 receptor activity antagonizing amount of a compound according to claim 1.

15. A method of treating schizophrenia in a patient in need thereof, comprising administering to the patient a schizophrenia treating effective amount of a compound according to claim 1.

16. A method of treating anxiety in a patient in need thereof, comprising administering to the patient an anxiety treating effective amount of a compound according to claim 1.

* * * * *